United States Patent [19]

Stoy et al.

[11] Patent Number: 4,631,188

[45] Date of Patent: Dec. 23, 1986

[54] INJECTABLE PHYSIOLOGICALLY-ACCEPTABLE POLYMERIC COMPOSITION

[75] Inventors: Vladimir A. Stoy, Princeton, N.J.; Milos Chvapil, Tucson, Ariz.

[73] Assignee: S.K.Y. Polymers, Ltd. (Kingston Technologies), Dayton, N.J.

[21] Appl. No.: 646,243

[22] Filed: Aug. 31, 1984

Related U.S. Application Data

[63] Continuation-in-part of Ser. No. 528,058, Aug. 31, 1983, abandoned.

[51] Int. Cl.$^4$ ..................... A61K 31/78; A61K 31/74
[52] U.S. Cl. ........................................ 424/81; 424/78; 525/294
[58] Field of Search ..................... 424/78, 81; 525/294

[56] References Cited

U.S. PATENT DOCUMENTS

| 4,279,795 | 7/1981 | Yamashita et al. | 260/29.6 RW |
| 4,331,783 | 5/1982 | Stoy | 525/294 |
| 4,337,327 | 6/1982 | Stoy | 525/280 |
| 4,370,451 | 1/1983 | Stoy | 525/294 |
| 4,379,874 | 4/1983 | Stoy | 524/27 |
| 4,420,589 | 12/1983 | Stoy | 525/93 |
| 4,423,099 | 12/1983 | Mueller et al. | 428/35 |

Primary Examiner—Leonard Schenkman

[57] ABSTRACT

There is disclosed a non-toxic physiologically-acceptable polymeric composition comprised of water insoluble, non-crosslinked polymeric compounds having a solubility parameter of between 9.2 and 15.5 (cal/cc)$^{\frac{1}{2}}$ dissolved in a polar, non-toxic water miscible solvent, which polymeric composition solidifies when placed in contact with living tissue by absorbtion of water and by gradual release of solvent into the surrounding tissue.

15 Claims, No Drawings

INJECTABLE PHYSIOLOGICALLY-ACCEPTABLE POLYMERIC COMPOSITION

This is a continuation-in-part of application Ser. No. 528,058 filed Aug. 31, 1983, abandoned.

FIELD OF INVENTION

This invention relates to a novel polymeric composition, and more particularly to a novel physiologically-acceptable polymeric composition and methods for using same.

BACKGROUND

Numerous polymeric compositions have been used as alloplastic implants in mammals for the following purposes:

(1) to augment tissue deficiency (e.g. in reconstructive facial surgery, mammary augmentation, etc.);

(2) to replace a functional body component, such as articular cartilage, bone, joint, blood vessel, trachea, dura matter, intraocular lens, etc.;

(3) to connect severed tissue (e.g. sutures and staples);

(4) to block certain ducts or passages (as in reversible sterilization by the Aldrich procedure); and (5) to provide a depot for sustained and controlled drug delivery, both local and systematic.

Hydrogels, or the water-swellable but water-insoluble polymers, are among the polymeric substrates which have been used as implantable plastics since they offer, inter alia, certain advantages, e.g. permeability for water-soluble compounds, good biological tolerance and controllable softness and flexibility.

Polymeric implants are formed in defined shapes and sizes as demanded by the specific application. Such preshaped forms have several disadvantages. Most significantly, the applications require surgical procedures. Secondly, a polymeric implant, as a rule, is encapsulated by collagenous tissue capsule and is not integratable into surrounding tissue; porous polymeric implants may be connected to surrounding tissue by in-growing cells, however, such porous polymeric implants are often prone to calcification, etc. Thirdly, the size and shape of the polymeric implant must be determined in advance and any changes of size and shape are affected by re-implantation.

Initial attempts to utilize solidifying compositions were directed to applications, such as dental filling materials, acrylic bone cements, and tissue adhesives based on polyurethanes and alpha-cyanoacrylates. Subsequently, research was directed to solidifying reactive systems. Initially, soft polysiloxane gels were used which do not solidify but which are, to some extent, injectable while preserving some gel-like properties. Such polysiloxane gels are maintained in place by granulation of the surrounding tissue rather than solidification and suffer from the disadvantages of containing low-molecular weight compounds, such as cyclic oligomers, which slowly migrate into the organism.

More recent attempts regarding solidifying compositions utilized an aqueous solution of purified bovine collagens which are injected into the tissue and which gelatinate when heated above 37° C. by collagen transition into fibrilar form without presence of low molecular weight toxic components. Collagen itself, however, is reactive and is gradually degraded by enzymatic reaction and is resorbed after a period of time. Thus, such a gelatinous implant is only a temporary replacement of a pre-formed implant which may be subsequently replaced by natural tissue. There is little control over such natural replacement, and unsatisfactory results occur in many instances.

OBJECTS OF THE INVENTION

An object of the present invention is to provide a novel solidifying physiologically-acceptable polymeric composition for implantation.

Another object of the present invention is to provide a novel solidifying physiologically-acceptable polymeric composition permitting of injectable implantation.

Still another object of the present invention is to provide a novel solidifying physiologically-acceptable polymeric composition obviating surgical implantation.

A further object of the present invention is to provide a novel solidifying physiologically-acceptable polymeric composition formed of non-toxic materials.

Still yet another object of the present invention is to provide a novel solidifying physiologically-acceptable polymeric composition inert to enzymatic attack.

SUMMARY OF THE INVENTION

These and other objects of the present invention are achieved by the use of a non-toxic physiologically-acceptable polymeric composition comprising water insoluble, non-crosslinked polymeric compounds having a solubility parameter between 9.2 and 15.5 $(cal/cc)^{\frac{1}{2}}$ dissolved in a polar, non-toxic water miscible solvent, which polymeric composition solidifies when placed in contact with living tissue by absorption of water and by gradual release of solvent into the surrounding tissue.

DETAILED DESCRIPTION OF THE INVENTION

The polymeric compounds suitable for the present invention are the water insoluble, non-crosslinked polymers and compolymers having a solubility parameter of between about 9.2 and 15.5 $(cal/cc)^{\frac{1}{2}}$, preferably between 10 to 13.5 $(cal/cc)^{\frac{1}{2}}$ See J. Paint Technol. 42,76 (1970).

1. The polymeric compound must be insoluble in water or blood serum below temperature of about 50° C., and advantageously below 100° C.;

2. The polymeric compound must be free of toxic low-molecular components, such as residual monomers, residual initiators, stabilizers or other additives in concentration which could be harmful;

3. The polymeric compound must be soluble in the solvent or solvent system at temperature below about 40° C.; and 4. The polymeric compound in solution and after injection results in an integral form of polymer containing between 25 to 95% by weight water, preferably between 45 to 95% by weight water. Examples of such polymeric compounds are: polymers and copolymers of acrylonitrile, particularly copolymers with other derivatives of acrylic acid, such as acrylamide, N-substituted acrylamide, acrylhydrazide, N-substituted acrylhydrazide, glutarimide, vinylsulfonate acid, acrylic acid and its salts; polyvinylacetate, its copolymers and particularly poly (vinylacetate-co-vinylalcohol); linear or slightly branched polymers and copolymers of 2-hydroxyethyl acrylate and methylacrylate; poly (N-vinyliminocarbonyl); and polycondensates and polyadducts, such as poly(oxyethyleneoxy carbonylimino-1,3- phenyleniminocarbonyl); poly(oxy-1,4-phenylensulfonyl-1,4-phenylene), poly(imino(1-oxoundecamethylene); poly(pyromellitic dianhydride-co-aromatic amines), or polymaic acid. Preferably such polymeric compounds are those which are soluble in dimethylsulfoxide (DMSO) but insoluble in water, as more fully hereinafter discussed.

Particularly advantageous polymeric compounds are those containing at least 2% nitrile groups, such as the polacrylonitrile and copolymers of acrylonitrile with various, particularly hydrophillic, comonomers. A particularly advantageous acrylonitrile copolymer is produced by the partial acid-catalyzed hydrolysis of a polymer containing at least 85 molar percent acrylonitrile units. Polyacrylonitrile and its copolymers, if coagulated from solution of sufficiently high viscosity, forms pseudo-hydrogels (or "aquagels"). The aquagel contains up to about 75% of water, more usually 30 to 60% of water. The water acts as a plasticizer, even if the polymer itself is non-swellable and essentially hydrophobic* an unlimited time period. Such an aquagel thus formed in tissue is a semirigid material suitable, for example, for facial bone augmentation.

*The water content is not in equilibrium as is the case with true hydrogels. Once the polymer is "dried", the resulting polymeric material cannot regain its original water content. The poly-acrylonitrile-type polymers when coagulated in tissue maintain their water content for essentially.

Hydrogels suitable for the invention are copolymers containing both hydrophilic and hydrophobic groups, such as vinylacetate-vinylalcohol or acryonitrile-acrylamide. More particularly suitable are copolymers in which both hydrophobic and hydrophilic groups are organized in continuous sequences, or block copolymers, such as described in U.S. Pat. No. 4,379,874, U.S. Pat. No. 4,420,589; U.S. Pat. No. 4,331,783; U.S. Pat. No. 4,337,327; and U.S. Pat. No. 4,370,451 (incorporated herein by reference) and which are particularly suited for the present invention.

The solvent or solvent system of the present invention for the above polymeric compounds should be polar, miscible with water and non-toxic. Preferred solvents for the present invention are the non-toxic water-miscible solvents having a molecular weight below about 200, exhibiting moderate to strong hydrogen-bonding capability and having a preferred solubility parameter between 10 and 15 $(cal/cc)^{\frac{1}{2}}$ for moderately H-bonding and between 11 and 20 $(cal/cc)^{\frac{1}{2}}$, e.g. between 12.5 to 17) for stronger H-bonding. Examples of such solvents are dimethyl sulfoxide (DMSO), glycerol, glycerol monoacetate, glycerol diacetate (diacetin), methanol, ethanol, propanol, iso-propanol, cyclic ethylene carbonate, cyclic propylene carbonate, dimethyl formamide, tetramethylene sulfoxide, N—N-diethylacetamide, N,N,-dimethylacetamide, ethylene glycol, propylene glycol, triethylene glycol and diethylene glycol and mixtures thereof.

The polymeric compound is admixed with the solvent in a concentration of from about 0.1 to 50% by weight, such that the resulting polymeric solution when in contact with water forms an integral solid (homogeneous or porous), and in no event forms a dispersion of solid polymer particles. In other words, the polymeric solution coagulates rather than precipitates when its contacts water. Such coagulation property is related to the solution viscosity, which is, in turn, determined by the molecular weight of the polymeric compound, its concentration and temperature. The viscosity of these compositions ranges from about 15 centipoises to about 20,000 centipoises. The concentration of the polymeric compound with solvent suitable for an injectable polymeric composition decreases with increasing molecular weight of the polymeric compound. Coagulation of the polymeric compound in contact with water is reversible, and is a purely physical process without any associated chemical change in the polymeric compound. The coagulated polymeric compound can be redissolved in the same or a similar solvent.

For certain applications, to modify mechanical properties of the resulting polymer and to provide opacity, it is desireable to add as a filler up to 50% by weight of an inorganic material in powder form to the polymeric composition. Such inorganic filler materials include calcium sulfate, barium sulfate, apatite, hydroxyapatite, aluminum hydrate and silicon dioxide.

The polymeric composition of the present invention may also include a biologically active substance to effect certain results, e.g. thrombin may be added to effect coagulation at the injected site, collagen may be added to provide a support site, etc. Advantageously, any such biologically active substance should be substantially soluble in the solvent or solvent system but essentially insoluble in water.

The solidification of a polymeric form upon injection of the polymeric composition solution into the tissue and without damage to the surrounding tissue is surprising since it is known that cell membranes are highly sensitive to the osmotic pressure imposed by a difference in concentrations of water-soluble compounds within and outside the cell. The osmotic equilibrium can also cause dehydration of cells which is equally damaging. Yet the cells survive the solidification of the resulting polymeric form even directly in intercellular space.

One possible explanation of such a finding is that the outermost layer of solution coagulates by intercellular liquid, having an equilibrium content readily replenished via the lymphatic system. The polymer "skin" thus formed takes over the major part of the concentration gradient. In other words, the barrier of the coagulated polymers controls the water and solvent permeation rates before a substantial pressure gradient across the cell wall can be established. This hypothesis, however, is not to be construed as limiting this invention.

The polymer solutions can be used in various medical situations. Typically, the polymeric composition or solutions yielding hydrogel upon the coagulation by the tissue fluids can be injected intradermally (i.d.) or subcutaneously (s.c.) to remove cosmetic skin defects or adjust facial contours (e.g. acne or pox scars, wrinkles, etc.) Most suitable for this particular application is a polymeric solution formed of from 5 to 25% by weight of a multiblock copolymer of acrylonitrile and/or acrylic acid, such as described, in the aforementioned U.S. Pat. No. 4,379,874, dissolved in dimethylsulfoxide and more particularly, 7.5 to 12.5% by weight. Such a resulting polymeric form exhibits a swelling capacity of from 50 to 97%, advantageously 70 to 92% in equilibrium with water.

The advantage of such specific formulation for this particular field of use is that the subcutaneously or intradermally injected polymeric solution does not solidify instantaneously, but can be shaped by pressure on skin several minutes following injection. This allows for contour adjustment without reinjection. Another advantage is that the hyrogel interpenetrates tissue cells without prevalent tissue reactions, such as encapsulation or fibrosis. Therefore, the repaired site remains soft and of constant size and shape without hardening or constriction in the course of time. The solidified hydrogel is embedded in intercellular spaces so that it is firmly anchored and cannot migrate. Finally, the hydrogel is enzymatically stable and does not degrade nor can it be resorbed.

True hydrogels (swelling to an equilibrium in contact with water) are particularly advantageous for replacement and augmentation of soft tissue, as a filler of body cavities and the like. Such a hydrogel is elastic with elasticity increasing with increasing water content. Additionally water uptake compensates for loss of solvent. The resulting hydrogel formed in the tissue may have a lower or higher volume than the injected solution, depending upon the solution concentration and the final (equilibrium) swelling of the hydrogel.

Formulations of similar compositions are also useful as fillers or blocks of ducts or cavities. In this case, the polymeric composition as solution is injected into a duct or cavity wall. The resulting polymeric form is not embedded in the intercellular space, but is clearly separated from the tissue. It is important for the polymeric form to entirely fill the duct or cavity. Therefore, the resulting polymeric form or material must not shrink upon solidification. On the contrary, mild expansion of the polymeric form or material is advantageous. This is achieved by selecting the appropriate polymeric form with appropriate water uptake or by adjusting the polymeric concentration in the polymeric solution or a combination of both. Generally, the volume fraction of polymeric compound in the polymeric solution is to be equal or higher than in the final hydrogel. Examples of uses of such solutions are in connection with reversible male or female sterilization, i.e. injection of the polymeric composition into the vas deferens or Fallopian tubes, respectively.

Another use of the injectable polymeric composition or solution is in connection with the reinforcement or the strengthening of deficient tissues, such as tendons, joint capsules, ligaments or blood vessel walls. The formulations useful in this field are those yielding hydrogels or aquagels with medium water content (20 to 65% of water) and high mechanical strength.

Still another use of the polymeric composition or solution of the present invention is the connection of severed tissues by injection into both tissue parts simultaneously or consecutively of such a polymeric composition or solution. The aquagels or hydrogels with moderate swelling are advantageous because contraction during solidification helps to hold the severed parts firmly yet gently together. Such a use is particularly desirable for connecting very soft tissue where sutures or surgical staples cannot be used.

Injection of the polymeric composition can be used also for strengthening and reinforcing soft or lacerated tissue (such as liver or spleen), unable to hold sutures or staples. Soft tissue which has been reinforced in this manner can be surgically dissected without excessive bleeding.

Similar injectable polymeric compositions can be used for permanent connection between tissue and an alloplastic material, such as a plastic gate for peritoneal dialysis. Such permanent connection prevents penetration of infection along the tissue/plastic interface.

While the above mentioned compositions are exceptionally well-tolerated in a variety of applications, it has been found that, in some specific types of situations, some mild side effects can be associated with their use. Under such circumstances, a slightly modified form of these polymeric compositions which will substantially avoid such side effects can be used. These modified compositions can be obtained by the pre-dilution of the polymer with water or a water/alcohol solution. Another modification comprises the addition of a hydrophobic "skin forming" component. Often, it is advantageous to both pre-dilute and add a "skin forming" component. These modified compositions result in a polymeric composition that is even less likely to cause side reactions than the unmodified forms.

The side effects which may temporarily occur following subdermal or subcutaneous injection of the unmodified form are erythema (reddening of the injected site), temporary swelling (in addition to permanent volume change caused by polymer itself) and tissue reaction (inflammatory reaction occasionally in exceptionally high dosages of the unmodified form while prenecrotic states and, in rare, worst cases, local necrosis can occur).

All the above effects are temporary, and even injections which result in local necrosis ultimately heal so that after a certain time the sites could not be distinguished from those without the initial tissue reaction. However, investigation has revealed that (1) reaction was more severe in ventral than dorsal aspect of test animals, (2) reaction was more likely to be severe for intradermal rather than subcutaneous (s.c.), injection, while injection into internal ducts, veins or internal organs caused no observable problem, (3) reaction increased with increasing injected volume. While injection of volumes up to 0.2 ml in single injections s.c. showed few side effects, injections s.c. larger than 0.2 ml and i.d. larger than 0.05 ml caused effects with severity increasing with increasing dose.

Evaluation of these experiments reveals that these side reactions have two principal causes: damage of cells by osmotic shock and damage of cells by hydraulic shock.

It has been found that the osmotic shock can be diminished by pre-dilution of the solvent with water which decreases the concentration gradient of water across the cellular wall. In addition, the predilution by water accelerates the formation of a barrier between cells and the coagulated polymer. Such a barrier will diminish the osmotic shock by slowing the release rate of the solvent so that it can be more efficiently diluted by body fluids.

The effect of the solvent is lesser in locations with ample fluid supply, such as internal organs, ducts or blood vessels.

Polymers particularly suitable for use in combination with aqueous solvents are linear or slightly branched polymers and copolymers of 2-hydroyxethyl acrylate and methacrylate, which are quite soluble in aqueous ethanol, isopropanol, in aqueous glycerol, aqueous 1,2-propyleneglycol or in aqueous DMSO.

It has been found that aqueous solvents dissolve such polymers much better than an anhydrous solvent. The reason for this is believed to be the fact that the solvents break water associates so that activity of —OH groups in the cosolvent mixture is greater than in pure water. The maximum solubility for the polymer in a cosolvent mixture corresponds to a molar ratio of water to the non-aqueous cosolvent of about 1, though polymers are usually soluble in broad range of solvent compositions. For instance, poly (2-hydroxyethyl methacrylate) can be readily dissolved in solvents containing ethyl alcohol or DMSO and up to about 65 wt-% of water. Suitable amounts of aqueous solvent can be as high as 70% and preferably up to 55% when hydrophillic polyacrylates and polymethacrylates are used. When derivatives or co-polymers of polyvinyl alcohol are used, up to 60% is useful, preferably up to 50%. Nitrile-containing systems may be used with up to 40% aqueous solvent, preferably up to 30%.

Another feature of these polymers is their relatively slow coagulation when their solution is mixed with water. The spongeous polymer structure is formed relatively slowly, forming first very soft semiliquid gel which gradually sets into hydrogel capable of plastic deformation. This makes these polymers particularly well suited for application into stiff tissues and other environments where mechanical strength of the resulting hydrogel is not a primary consideration. Examples of such use include subcutaneous or intradermal injection to correct skin defects, such as acne scars or wrinkles.

Polymers with similar solubility characteristics and similar uses as the polymers above are polymers and copolymers of N-substituted acrylamides soluble in alcohols, glycerine or 1,2 propylene glycol but insoluble in water.

An example of such a polymer is the product of the reaction of poly (2,4-glutarimide) with octadecylamine and 3-aminopropylmorfolin, which is insoluble in water but soluble in aqueous glycerol.

Another group of compositions suitable for subcutaneous and intradermal applications are multiblock copolymers of acrylonitrile with predominant amount of acrylamide and advantageously other substituents such as methyl acrylate, acrylic acid or acrylate, or N-substituted acrylamide or acrylhydrazide. The content of acrylonitrile units is between 3 and 25%, advantageously between 5 and 15 mol %. Acrylamide units form at least 50% of the non-acrylonitrile units. Such copolymers can be prepared by acid- or acid base-catalyzed hydrolysis of polymers and copolymers of acrylonitrile, or more advantageously from block copolymers of acrylonitrile-glutarimide (described in U.S. Pat. No. 4,331,783) by reactions described in U.S. Pat. Nos. 4,337,327 and 4,370,451, the disclosures of which are incorporated by reference.

The molecular weight of such copolymers is advantageously kept low to keep viscosity of the solution low, for example, in the range of about 15 to 500 centipoises. A viscosity in the range of 45 to 300 centipoises is preferred for these applications. Typical molecular weight of such copolymers for subcutaneous or intradermal injections is between 50,000 to 150,000. Concentration of such polymers in injectable compositions is between 2 and 25 by weight, the lower concentration limit being suitable for higher molecular weight limit and vice versa. Such copolymers are preferably dissolved in DMSO, which can contain up to about 30% by wt. of water to diminish the osmotic shock.

The dilution of DMSO by water in the compositions containing the above described acrylonitrile-containing multiblock copolymer decreases the osmotic shock both directly (by decreasing concentration gradient of water between the cell and the solvent) and indirectly. The indirect effect consists in accelerated coagulation of the polymer to form the tissue-protecting barrier. This can be utilized particularly for injection into soft tissues, ducts, cavities and vessels where effects of hydraulic pressure are not significant.

It has now been found that certain polymer solutions coagulate in contact with water in a particularly advantageous manner. Solutions of mixtures of a larger portion of hydrophilic polymer and a smaller portion of hydrophobic polymer form fine surface skin in contact with water. The skin has low permeability and thereby effectively protects surrounding tissue from osmotic shock. The initially-formed skin is very thin (thinner films are produced by less permeable compositions) so that it does not substantially increase the resistance of the tissue to the penetration of the solution. It is believed that the fast surface coagulation diminishes the osmotic shock without undesirable simultaneous increase in hydraulic pressure during injection.

Typical aqueous solutions with such coagulation behavior are compositions of highly hydrophobic multiblock copolymers of acrylonitrile mixed with polacrylonitrile as described in U.S. Pat. No. 4,379,874, dissolved in DMSO. Another example is a mixture of hydrophilic vinyl alcohol/vinyl acetate opolymer with polyvinyl acetate. The solvents of the above composition can be diluted with water so that viscosity of the solution does not exceed the preferred values set forth above and the polymer separation does not take place in the solution. The dilution with water accelerates the skin formation and diminishes osmotic shock still further.

EXAMPLE 1

Multiblock acrylonitrile hydrogel was prepared by partial hydrolysis of polyacrylonitrile (MW-150,000) dissolved in a mixture of sulphuric and phosphoric acid at 35° C. After the desired conversion hydrolysis was reached, the polymer solution was extruded into an excess of water and the coagulated hydrogel was thoroughly washed and then dried. Dry polymer was dissolved in DMSO to form a solution of 10% by weight of the polymer, cast into thin foil and coagulated with water. After thoroughly washed, the hydrogel contained 90% of weight of water. Sections of hydrogel film were soaked in DMSO diluted with water to 100%, 75% and 25% of DMSO. Then 0.5 gram portions of the DMSO-swollen gel were implanted subcutaneously in the abdominal region of rats through a small skin incision. Skin reaction was observed twice daily for 3 days, at which time it was sampled for histological evaluation.

The multiblock hydrogel was also dissolved in DMSO to form solutions of 5% by weight, and 10% by weight of the polymer.

Poly (2-hydroxyethyl methacrylate (PHEMA)), prepared by polymerization of highly purified monomer, was dissolved in DMSO to form a 10% by weight solution.

The foregoing solutions were injected subcutaneously into abdominal region of rats in volumes ranging from 0.1 to 0.5 ml.

As a control, DMSO undiluted and diluted with water to 75%, 50% and 25% by volume of DMSO was injected into the abdominal region of rats (0.5 ml subcutaneously).

The results show that:

(1) DMSO imbibed in the hydrogel causes no adverse reaction, even for undiluted DMSO.

(2) The 10% solution of the same polymer in DMSO causes strong reddening (erythema) and tissue reaction for injections of volumes of 0.2 ml or more.

(3) 5% solution of the same polymer in DMSO causes mild erythema and minimal tissue reaction around a homogeneous hydrogel implant.

(4) 10% solution of PHEMA in DMSO causes no erythema and minimum tissue reaction around the spongy hydrogel.

(5) Injection of DMSO at a concentration of 75% or 100% causes strong erythema and tissue reaction resulting in necrosis.

The conclusion reached was that the polymer protects the tissue against solvent shock; lower solution viscosity is desirable (PHEMA and 5% versus 10% concentration of the acrylic hydrogel) to prevent side effects of hydraulic pressure resulting from injection.

EXAMPLE 2

The multiblock copolymer of acrylonitrile and acrylamide was prepared as described in Example 1 at 30° C. The lower conversion of hydrolysis caused that equilibrium water content to be 55% by wt. Ten wt. parts of the copolymer was dissolved in 90. wt. parts of DMSO. The solution was used in various experiments with the following results:

(1) 0.5 ml of the solution was injected into the uterine horn of a female rat through the uterine wall. The solution solidified into the firm yet flexible hydrogel bolus which blocked the Fallopian tube (and thus causing reversible sterility). Histological examination after 7,33 and 42 days showed no evidence of irritation of the mucous membrane or disruption of the epithelial lining.

(2) The same polymer solution was injected into dog liver in multiple injections of 0.5 ml each. The hydrogel solidifed in the soft liver tissue to form a barrier across one of the lobes. A lobotomy was then carried out essentially without bleeding and the resected liver healed without post-surgery complications.

(3) The same solution was injected in multiple doses of 0.2-0.5 ml each into lacerated muscle of a rabbit (gunshot wound). The hydrogel solidified in the tissue and bleeding was stopped. The subsequent healing proceeded without complications.

(4) The same solution was injected subcutaneously into the abdominal region of rats in doses of from 0.1 to 0.5 ml. The 0.1 ml injection caused erythema, while doses of 0.2 and higher caused strong erythema and same local tissue necrosis.

These results indicate that rapidly coagulating and viscous polymer solutions are suitable for injections into internal body cavities and soft and/or bleeding tissues while they are less suitable for injections into more rigid tissues such as skin.

EXAMPLE 3

Poly (2-hydroxyethyl methacrylate)(PHEMA), MW-90,000, was prepared by polymerization of purified monomer (HEMA) solution in water by a hydrogen peroxide initiator. The polymer was purified by reprecipitation from an alcoholic solution into ether and dried. Ten wt. parts of PHEMA was dissolved in 90 wt. parts of 50% aqueous ethanol and injected subcutaneously (s.c.) and intradermally (i.d.) into the abdominal region of a rat, a rabbit and a pig.

The injected volumes up to 0.2 ml s.c. and 0.1 ml i.d. caused no erythema and only negligible tissue reaction. The injected sites slowly diminished in volume until their size stabilized after several hours. The maximum swelling was observed between about 5 minutes and 2 hours, when the injection was still very soft and semiliquid. After several hours a well defined spongy-looking implant was formed which caused no tissue reaction. The decrease of the injected volume is advantageous for cosmetic applications because it prevents overcorrection.

The lack of erythema and tissue reaction illustrates the beneficial effect of the dilution of solvent with water and the resulting slow coagulation of the polymer.

EXAMPLE 4

A copolymer of acrylonitrile (93 mole %) and methylacrylate (7 mole %) MW=110,000, was hydrolized at 30° C. in solution in a mixture of phosphoric and sulfuric acids. When the desired conversion of hydrolysis was reached, the polymer was coagulated by water, washed and dried. Equilibrium swelling capacity of the hydrogel was 93.5% by wt. of water. The following two solutions were prepared from the hydrolyzate:

(A) Ten wt. parts of the polymer were dissolved in 90 wt. parts of 85% aqueous DMSO.

(B) 5 wt. parts of the hydrolyzate and 0.5 wt. parts of the starting acrylonitrile copolymer were dissolved in 95 wt. parts of DMSO. Solution A was a higher viscosity than Solution B and coagulates rapidly into clear, soft gel upon contact with water.

The final volume of gel is larger than the volume of the solution. Solution B, in contact with water, forms immediately a very thin opaque "skin" on the surface, while still liquid beneath.

The "skin" is initially very soft and weak but gradually increases in thickness until all of the solution is fully solidified into an opaque, flexible hydrogel. The volume of the final hydrogel is somewhat smaller than that of the original solution.

Both solutions A and B were injected s.c. into dorsal and ventral aspects of rats. Solution A was well tolerated up to 0.3 ml on the dorsal side and up to 0.2 ml on the ventral side, while solution B was tolerated up to 0.5 ml and 0.3 ml on the dorsal and the ventral side, respectively. The typical injected volume in a facial cosmetic application is up to 0.1 ml in a single injection.

Both solutions A and B could be formed for a time after injection by mild pressure across the skin, indicating that at least part of the injected solution is still liquid. Solution A solidified substantially faster than solution B.

What is claimed is:

1. A method of in situ formation of a solid polymer in a mammal, said method comprising:
    injecting into said mammal a physiologically-acceptable polymeric composition comprised of a polymeric compound dissolved in a water soluble, non-toxic polar solvent, said polymeric compound comprising a water insoluble, non-toxic non-crosslinked polymer or copolymer selected from the group consisting of polymers and copolymers of acrylonitrile, polyvinylacetate, copolymers of polyvinylacetate, linear or slightly branched polymers and copolymers of 2-hydroxyethylacrylate and methylacrylate, poly (n-vinyliminocarbonyl), polycondensates and polyadducts and having a solubility parameter of from about 9.2 to about 15.5 $(cal/cc)^{\frac{1}{2}}$.

2. The method of claim 1 wherein said polymeric compound is insoluble in blood serum below about 50° C.

3. The method of claim 2 wherein said polymeric compound is soluble in said solvent at temperatures below 40° C.

4. The method of claim 1 wherein said polymeric compound is a copolymer of acrylonitrile with a derivative of acrylic acid and selected from the group consisting of acrylamide, N-substituted acrylamide, acrylhydrazide, N-substituted acrylhydrazide, acrylic acid, acrylic acid salts, glutarimide and vinylsulfonate.

5. The method of claim 1 wherein said copolymer of polyvinylacetate is poly(vinylacetate-co-venylalcohol).

6. The method of claim 1 wherein said solvent has a molecular weight below about 200 and exhibits at least a moderate hydrogen bonding ability.

7. The method of claim 6 wherein said solvent is selected from the group consisting of dimethyl sulfoxide (DMSO), glycerol, glycerol monoacetate, glycerol diacetate (diacetin), methanol, ethanol, propanol, isopropanol, cyclic ethylene carbonate, cyclic propylene carbonate, dimethyl formamide, tetramethylene sulfoxide, N—N-diethylacetamide, N,N,-dimethylacetamide, ethylene glycol, propylene glycol, triethylene glycol and diethylene glycol and mixtures thereof.

8. The method of claim 6 wherein said solvent is dimethylsulfoxide.

9. The method of claim 8 wherein said polymeric compound is in a concentration of from 0.1 to 50 percent by weight.

10. The method of claim 1 wherein said water insoluble non-cross linked polymer contains at least 2 weight percent nitrile groups.

11. The method as defined in claim 1 wherein said acrylonitrile-containing copolymer is produced by the partial acid-catalyzed hydrolysis of a polymer containing at least 85 molar percent of acrylonitrile units.

12. The method as defined in claim 1 wherein said polymeric composition after injection results in a polymeric form containing from 25 to 99 percent by weight water.

13. The method as defined in claim 12 wherein said polymeric form contains from 45 to 95 percent by weight water.

14. The method as defined in claim 13 wherein said polymeric composition, after injection, results in a polymeric form containing from 50 to 99 percent by weight water.

15. The method as defined in claim 14 wherein said polymeric form contains 70 to 95 percent by weight water.

* * * * *